US00PP30334P2

(12) United States Plant Patent
Snijder

(10) Patent No.: US PP30,334 P2
(45) Date of Patent: Apr. 2, 2019

(54) ***PELARGONIUM* PLANT NAMED 'PEQZ0037'**

(50) Latin Name: *Pelargonium interspecific*
Varietal Denomination: PEQZ0037

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,691

(22) Filed: Apr. 9, 2018

(30) Foreign Application Priority Data

Oct. 23, 2017 (EM) ..... 2017/2676

(51) Int. Cl.
*A01H 5/02* (2018.01)

(52) U.S. Cl.
USPC ..... Plt./330

(58) Field of Classification Search
USPC ..... Plt./263.1, 324, 325, 330
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Pelargonium* plant named 'PEQZ0037' particularly distinguished by the dark red inflorescences held above the dark green foliage, very heat and drought tolerant with continuous color through the most extreme summer heat, and a well-branched spreading plant habit.

1 Drawing Sheet

Figure 1:
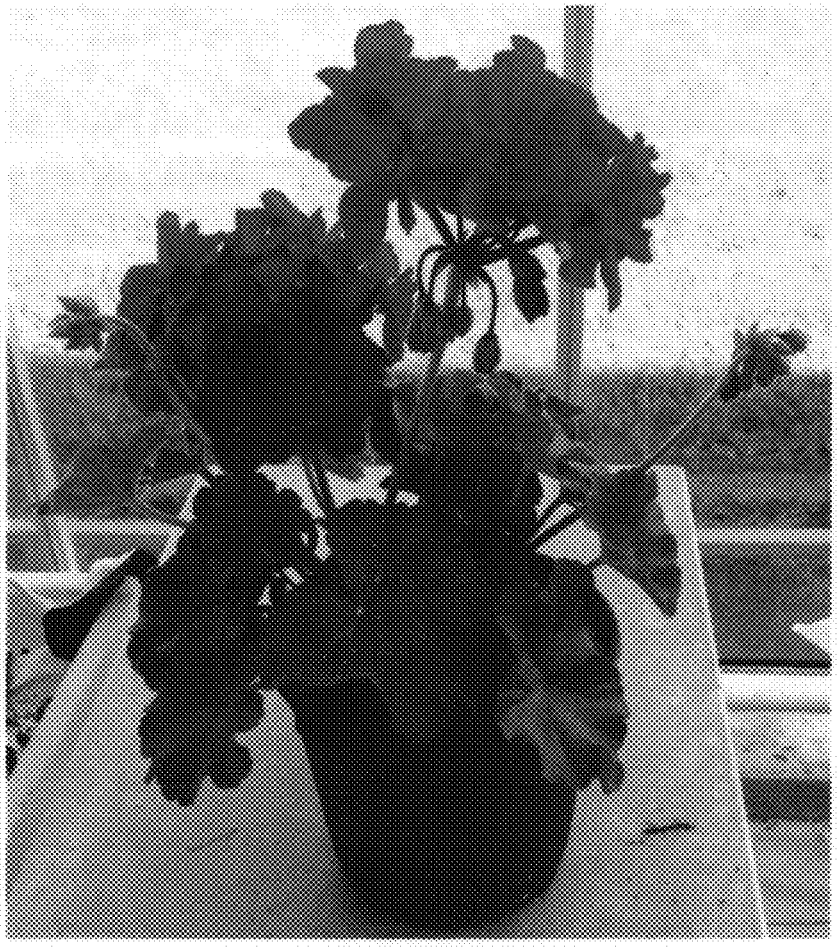

Latin name of the genus and species of the plant claimed: *Pelargonium interspecific.*
Varietal denomination: 'PEQZ0037'.

BACKGROUND OF THE NEW PLANT

The present invention comprises a new *Pelargonium*, botanically known as *Pelargonium interspecific*, and hereinafter referred to by the variety name 'PEQZ0037'.

'PEQZ0037' is a product of a planned breeding program. The new cultivar 'PEQZ0037' has dark red colored inflorescences with semi-double florets held above dark green foliage, very heat and drought tolerant with continuous color through the most extreme summer heat, on a well-branched spreading plant habit.

'PEQZ0037' originates from a hybridization in a controlled breeding program made in February 2013 in a greenhouse in Enkhuizen, The Netherlands. The female parent was an unpatented, proprietary plant of *P. interspecific* parentage, identified as '10972-2' with a larger plant size and lighter green foliage when compared to 'PEQZ0037'.

The male parent of 'PEQZ0037' was an unpatented, proprietary plant of *P.* x *hortorum* parentage, identified as 'PEZ-AY0450-04' with more orange red colored florets when compared to 'PEQZ0037'. The resultant seed was sown in January 2014.

'PEQZ0037' was selected as one flowering plant within the progeny of the stated cross in June 2014 in a greenhouse in Enkhuizen, The Netherlands.

The first act of asexual reproduction of 'PEQZ0037' was accomplished when vegetative cuttings were propagated from the initial selection in July 2014 in a greenhouse in Enkhuizen, the Netherlands.

BRIEF SUMMARY OF INVENTION

Horticultural examination of plants grown from cuttings of the plant initiated in August 2014 in Enkhuizen, The Netherlands, and continuing thereafter, has demonstrated that the combination of characteristics as herein disclosed for 'PEQZ0037' are firmly fixed and are retained through successive generations of asexual reproduction.

'PEQZ0037' has not been observed under all possible environmental conditions. The phenotype may vary significantly with variations in environment such as temperature, light intensity, and day length.

A Plant Breeder's Rights for this cultivar was applied for in the European Union on Oct. 23, 2017, No. 2017/2676. 'PEQZ0037' has not been made publicly available prior to the effective filing date of this application, notwithstanding any disclosure that may have been made less than one year prior to the effective filing date of this application by the inventor or another who obtained 'PEQZ0037' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0037' with colors being as true as possible with an illustration of this type. The photographic drawings show in FIG. 1, 1 flowering plant of the new variety and in FIG. 2, a close-up of an inflorescence.

DETAILED BOTANICAL DESCRIPTION

The plant descriptions and measurements were taken in Enkhuizen, The Netherlands in late October 2017 under natural light. These plants were approximately 22-24 weeks old and were grown in a 3 gallon pots, in an outdoors trial.

Figure 2:
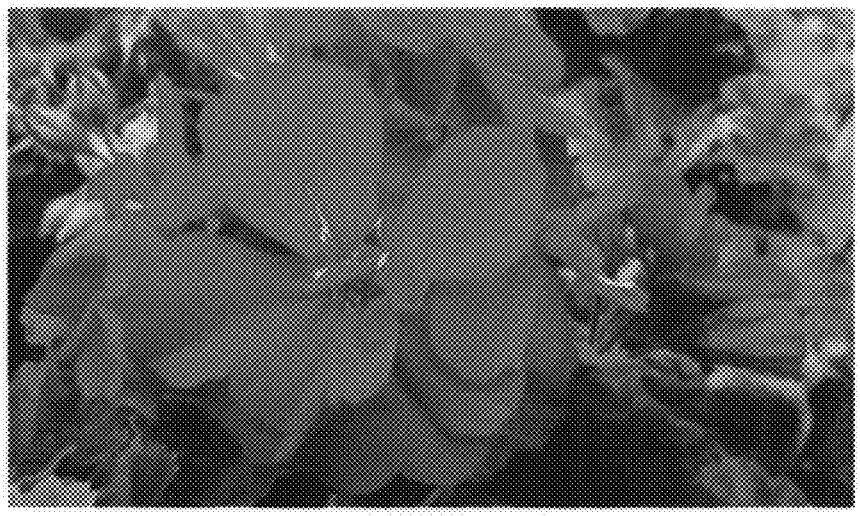

The plant shown in FIG. 1 was about 14 weeks old growing in a 4 inch pot in a greenhouse. The photographs were taken in April 2017.

Color references are made to The Royal Horticultural Society Colour Chart (R.H.S.) 2001.

TABLE 1

DIFFERENCES BETWEEN THE NEW VARIETY 'PEQZ0037' AND A MOST SIMILAR VARIETY

| | 'PEQZ0037' | 'Clip Velred' (U.S. Plant Pat. No. 20,532) |
|---|---|---|
| Length of peduncle: | Shorter | Longer |
| Peduncle: anthocyanin coloration of middle third | Weak | Very strong |

Plant:

*Form, growth and habit.*—Upright, outwardly spreading and rounded growth habit, heat and drought tolerant with continuous color through the most extreme summer heat, edema tolerance, well-branched plant habit.

*Plant height.*—27-29 cm.

*Plant height (inflorescence included).*—30-36 cm.

*Plant width.*—45-47 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 137A with a slightly lighter mottling.

*Immature leaf, lower surface.*—Closest to RHS 138B.

*Mature leaf, color upper surface.*—Closest to RHS 137A with slightly lighter mottling.

*Mature leaf, color lower surface.*—Closest to RHS 137C. Veins 146D.

*Length.*—7-8 cm.

*Width.*—8-9 cm.

*Shape.*—Cordate, a bit tridentate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 144A at base of leaf.

*Color of veins, lower surface.*—RHS 145B at base of leaf.

*Pattern of veining.*—Palmate.

*Petiole color.*—RHS 143C.

*Petiole length.*—6.8-12.9 cm.

*Diameter of petiole.*—0.3 cm.

*Texture.*—Pilose, hirsute, glandular hairs.

Stem:

*Quantity of branches.*—7-9.

*Color of stem.*—Between RHS 145A and RHS 145B.

*Length of stem.*—9-15 cm.

*Diameter.*—0.6-1.1 cm.

*Length of internodes.*—1.0-2.6 cm.

*Texture.*—Sparsely hirsute, pilose, glandular hairs.

Peduncle:

*Color of peduncle.*—RHS 146A.

*Length of peduncle.*—10-17 cm.

*Peduncle diameter.*—0.35-0.8 cm.

*Texture.*—Hirsute, glandular hairs.

Pedicel:

*Color of pedicel.*—RHS N92 with RHS 140C influences.

*Length of pedicel.*—1.5-2.6 cm.

*Diameter of pedicel.*—0.15-0.2 cm.

*Texture.*—Sparsely pilose, glandular hiars.

Bud (just before opening):

*Color.*—Closest to RHS 60B and RHS 61B.

*Length.*—1.3 cm.

*Width.*—0.5-0.7 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—10-19, with immature umbels in various stages.

*Fragrance.*—None.

*Umbel diameter.*—10-11 cm.

*Umbel depth.*—6.5-7.5 cm.

Corolla:

*Form.*—Semi-double.

*Number of petals.*—Up to 14.

*Diameter of flower.*—About 3-4.3 cm.

*Depth of flower.*—1.5-2.0 cm.

*Color upper petals, upper surface.*—Closest to RHS 45B but brighter and deeper, up to RHS 46A veining.

*Color upper petals, lower surface.*—Closest to RHS 45B but brighter and deeper, veins RHS 45D.

*Length of upper petals.*—2.2-2.9 cm.

*Width of upper petals.*—1.7-1.9 cm.

*Color lower petals, upper surface.*—Closest between RHS 46A and B but brighter and deeper.

*Color lower petals, lower surface.*—Closest to RHS N57A but brighter and deeper.

*Length of lower petals.*—0.7-1.2 cm.

*Width of lower petals.*—0.9-1.3 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—7.

*Color of sepals.*—RHS 144A mottled with anthcyanins of about RHS 178B.

*Length of sepals.*—1-1.2 cm.

*Width of sepals.*—0.5 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.2 cm.

*Style color.*—RHS 145D.

*Style length.*—0.7 cm.

*Stigma color*.—Closest to RHS 157A.
*Ovary color*.—Between RHS 145B.
*Ovary length*.—0.4-0.5 cm.
*Ovary diameter*.—0.2 cm.

Androecium:

*Number of stamens*.—3-6.
*Color of filaments*.—Whiter than RHS 155D.
*Length filaments*.—0.7 cm.
*Anther color*.—Near RHS 187A.
*Length of anthers*.—0.2 cm.
*Color of pollen*.—Near RHS 21A.
*Pollen amount*.—Normal.
*Fertility/seed set*.—Has not been determined to date.
*Disease/pest resistance*.—Has not been determined to date.

What is claimed is:

1. A new and distinct variety of *Pelargonium* plant named 'PEQZ0037' substantially as illustrated and described herein.

* * * * *